(12) United States Patent
Carson

(10) Patent No.: US 10,328,214 B2
(45) Date of Patent: Jun. 25, 2019

(54) SYRINGE GUIDE AND METHOD FOR ITS USE

(71) Applicant: William Carson, Summersville, WV (US)

(72) Inventor: William Carson, Summersville, WV (US)

(*) Notice: Subject to any disclaimer, the term of this patent is extended or adjusted under 35 U.S.C. 154(b) by 12 days.

(21) Appl. No.: 15/282,316

(22) Filed: Sep. 30, 2016

(65) Prior Publication Data
US 2018/0093049 A1 Apr. 5, 2018

(51) Int. Cl.
A61M 5/00 (2006.01)
A61M 5/46 (2006.01)
A61M 5/31 (2006.01)

(52) U.S. Cl.
CPC ............... *A61M 5/46* (2013.01); *A61M 5/31* (2013.01)

(58) Field of Classification Search
CPC .......... A61M 2005/1585; A61M 25/02; A61M 5/425
See application file for complete search history.

(56) References Cited

U.S. PATENT DOCUMENTS

| 5,241,969 | A | 9/1993 | Carson et al. |
| 8,517,985 | B2* | 8/2013 | Wei ................ A61M 5/46 604/117 |
| 8,521,257 | B2 | 8/2013 | Whitcomb et al. |
| 8,628,498 | B2 | 1/2014 | Safabash et al. |
| 8,641,674 | B2 | 2/2014 | Bobroff et al. |
| 2005/0137525 | A1* | 6/2005 | Wang ............ A61M 37/0015 604/93.01 |
| 2009/0270722 | A1 | 10/2009 | Floyd et al. |
| 2011/0028847 | A1 | 2/2011 | Whitmore, III et al. |

FOREIGN PATENT DOCUMENTS

EP 0654244 7/1994

* cited by examiner

Primary Examiner — Rebecca E Eisenberg
(74) Attorney, Agent, or Firm — Trego, Hines & Ladeneim, PLLC

(57) ABSTRACT

A syringe guide includes: a syringe receiver including a receptacle configured to retain a syringe therein; a depth guide defining a reference surface; and a depth adjustment mechanism interconnecting the syringe receiver and the depth guide, and operable to change a distance between the receptacle and the reference surface.

27 Claims, 16 Drawing Sheets

SYRINGE GUIDE AND METHOD FOR ITS USE

BACKGROUND OF THE INVENTION

This invention relates generally to syringes and more particularly to a guide apparatus for use in connection with injecting or aspirating with a syringe.

Healthcare professionals such as doctors, nurses, and aids are challenged with administration of injectables or aspirating with a hand held syringe with accuracy. A tremulous healthcare worker, or pain or fear in the patient causing the patient to flinch, can make it difficult for a stable and accurate injection or aspiration. Further, it is often difficult for the doctor to accurately position the needle either at a particular angle or depth to inject or aspirate an area such as the hand or knee, which requires a high degree of accuracy, steadiness and in some cases, repeatability.

Typically, the doctor relies on an opposing hand, a steady patient or similar methods to deliver an injection with accuracy. Similarly the doctor must rely on visual means for depth of needle and angular deliveries of medicine. While these methods are usually adequate, instances where the patient is in pain and/or nervous makes the task much more difficult for the doctor. Typically, in a lot of cases a second person may be required to steady the patient while the doctor performs the injection. Typically as in the case of an injection in the arm or larger muscular areas, accuracy is second to making sure that the medicine enters into the muscle. However in the case where accuracy is of primary concern, if the end of the needle is not precisely in place at the time of delivery, a second injection may be required, or worse, the medicine has an adverse effect.

While drawing off fluid from a joint (a knee for example) the syringe is changed one or more times during the procedure. This is currently done by the healthcare provider reaching down with the non-dominant hand and grasping the hub of the needle. This risks inadvertent removal of the needle as the syringe is twisted for removal and possible contamination of the sterile field.

Over penetration of a needle, as in an intramuscular injection, or "feeling around" in an attempt to find the correct needle target, can cause patient discomfort and/or damage to surrounding tissues. Medications injected into the wrong tissue can alter pharmacokinetics and damage unintended tissues, and in some circumstances could be lethal.

Certain types of medications, such as vaccines and collagenase injections, require multiple punctures at varied depths. However, these procedures are more uncomfortable than simple injections. After the first needle prick the patient may retract, and the depth can vary widely.

Accordingly, there is a need for an apparatus that allows for a stable platform that allows for accurate angular and depth delivery of medicine and similarly allows for the ability to remove the empty (or full) syringe while leaving the needle in place and subsequently replacing the empty (or full) syringe.

BRIEF SUMMARY OF THE INVENTION

This need is addressed by an adjustable guide for a syringe.

According to one aspect of the technology described herein, a syringe guide includes: a syringe receiver including a receptacle configured to retain a syringe therein; a depth guide defining a reference surface; and a depth adjustment mechanism interconnecting the syringe receiver and the depth guide, and operable to change a distance between the receptacle and the reference surface.

According to another aspect of the technology described herein, a method of administering a needle to a patient at a controlled depth includes the steps of: inserting a syringe having a needle attached thereto into a receptacle of a syringe guide, wherein the syringe guide includes: a syringe receiver that defines the receptacle; a depth guide defining a reference surface; and a depth adjustment mechanism interconnecting the syringe receiver and the depth guide; determining a desired protrusion of the needle beyond the reference surface; setting the desired protrusion of the needle using the depth adjustment mechanism; and penetrating the patient's body with the needle at a selected site, whereby penetration of the needle into the patient's body is limited by the reference surface.

BRIEF DESCRIPTION OF THE DRAWINGS

The invention may be best understood by reference to the following description taken in conjunction with the accompanying drawing figures, in which.

DETAILED DESCRIPTION OF THE INVENTION

Figure 1:
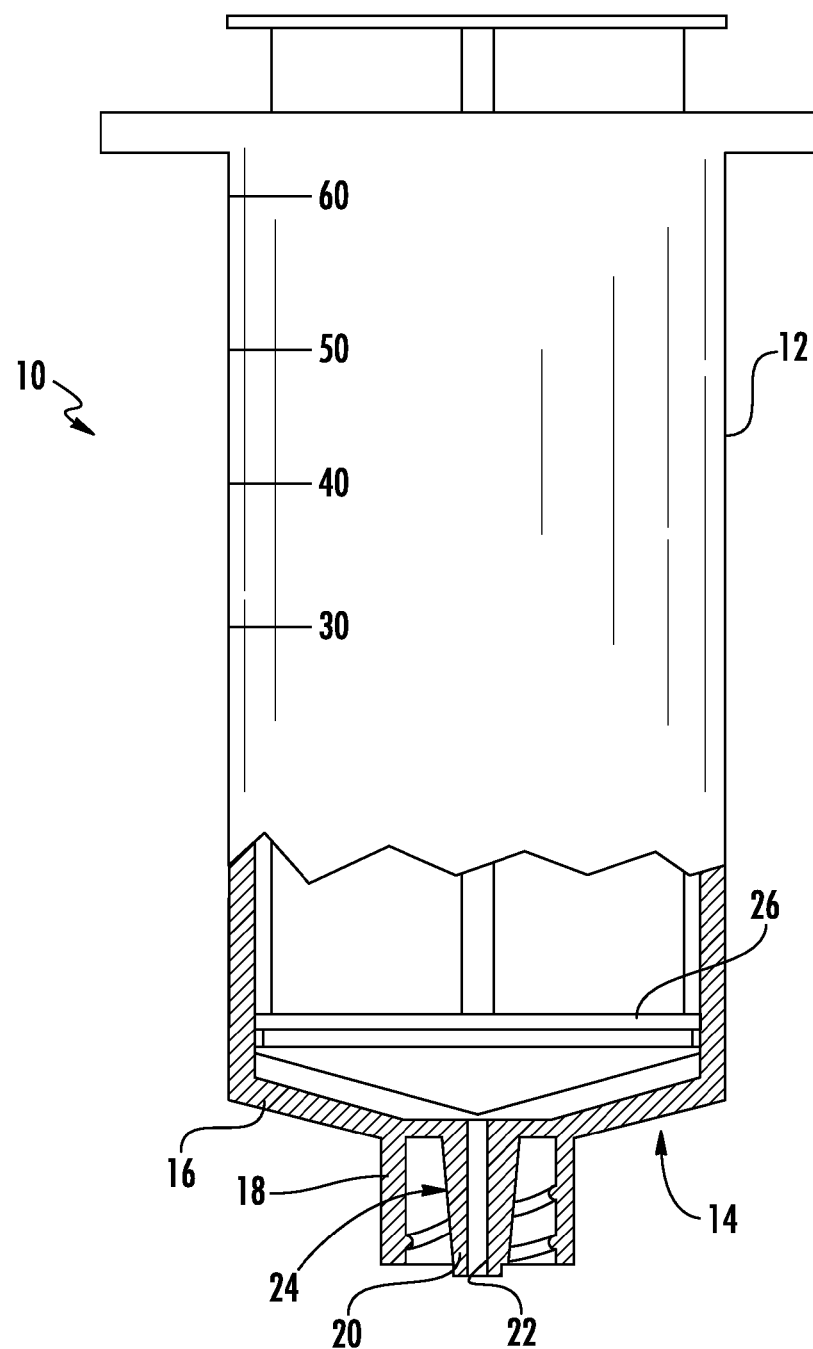
FIG. 1 is a schematic partially-sectioned view of a prior art syringe.

Referring to the drawings wherein identical reference numerals denote the same elements throughout the various views, FIG. 1 illustrates a typical commercially available syringe 10. The syringe 10 has a cylindrical sidewall 12 and terminates in an end wall structure 14 including a conical end wall 16 with a cylindrical needle boss 18 extending therefrom. A needle fitting 20 is disposed within the needle boss 18 and has an orifice 22 passing therethrough. An outer surface 24 of the needle fitting 20 is tapered at a predefined angle. The syringe 10 receives a plunger 26 therein.

Figure 2:
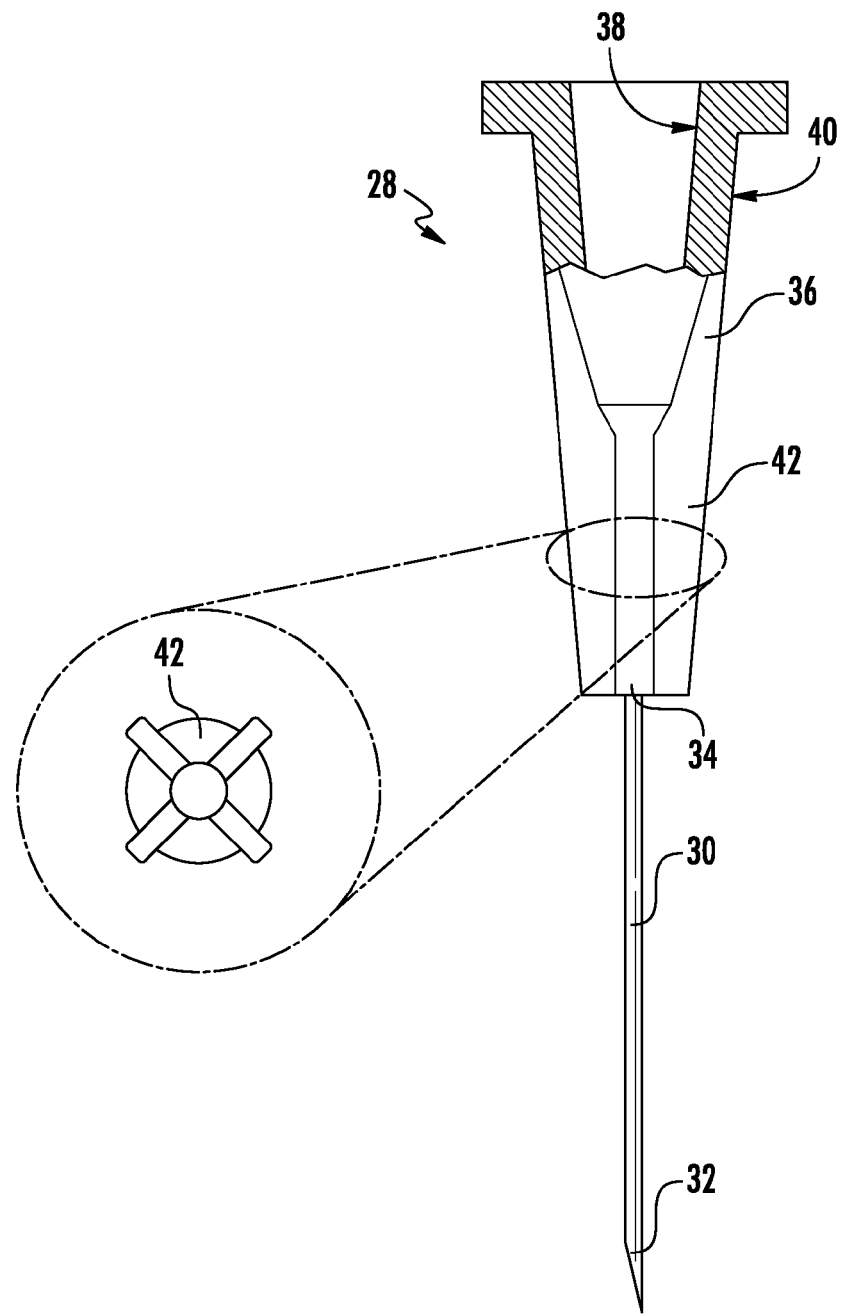
FIG. 2 is a schematic partially-sectioned view of a prior art needle assembly.

FIG. 2 illustrates a typical needle assembly 28 comprising a hollow, pointed needle 30 having an exposed distal end 32 and a proximal end 34 received in a needle hub 36. The needle hub 36 is an elongated body having an inner surface 38 which is tapered at a predefined angle equal or similar to the angle of the outer surface 24 of the needle fitting 20, and an outer surface 40. The outer surface 40 may include a feature configured for the application of torque to the needle hub 36, for example the illustrated cruciform or square cross-sectional shape portion 42.

Figure 3:
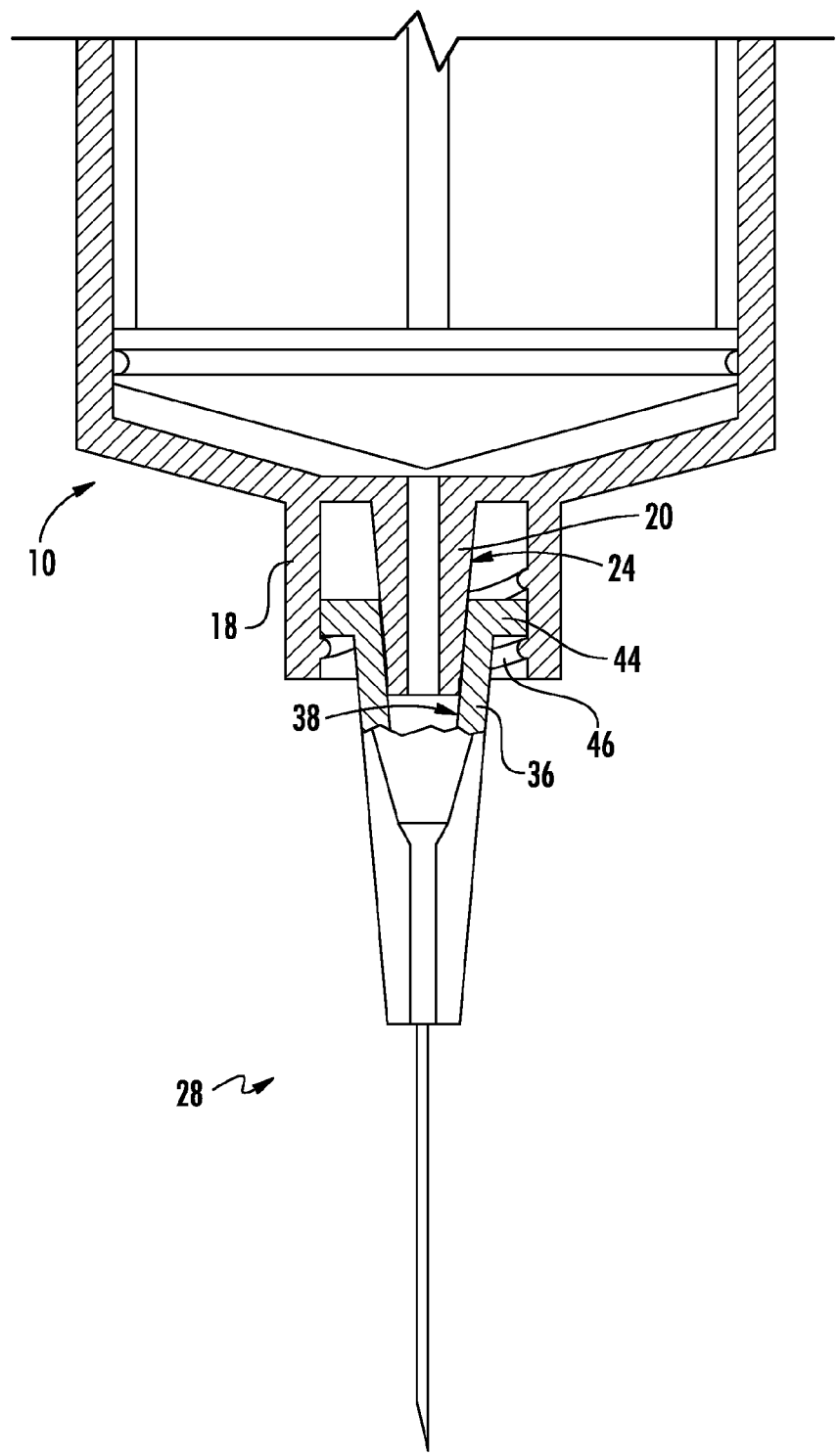
FIG. 3 shows the needle assembly of FIG. 2 connected to the syringe of FIG. 1.

FIG. 3 shows the needle assembly 28 connected to the syringe 10. More specifically, the needle hub 36 fits over the needle fitting 20 with the inner surface 38 engaged in a friction fit with the outer surface 24 of the needle fitting 20. The fit between the needle hub 36 and the needle fitting 20 is thus analogous to a taper fit as used in machine tools. Optionally, the needle hub 36 may be further retained by a mechanism such as the illustrated tabs 44 which engage female threads 46 formed in the needle boss 18.

The type of needle assembly 28 described above, and the complementary syringe end wall structure 14 are commercially available, for example under the LUER-LOK brand. Generally herein this will be referred to as a "taper-fit" needle assembly. Commercially, the end wall assembly 14 and the needle hub 36 have common standardized mating dimensions, while needles of different diameter (i.e. "gauge size"), length, and tip configuration may be provided.

Figure 4:
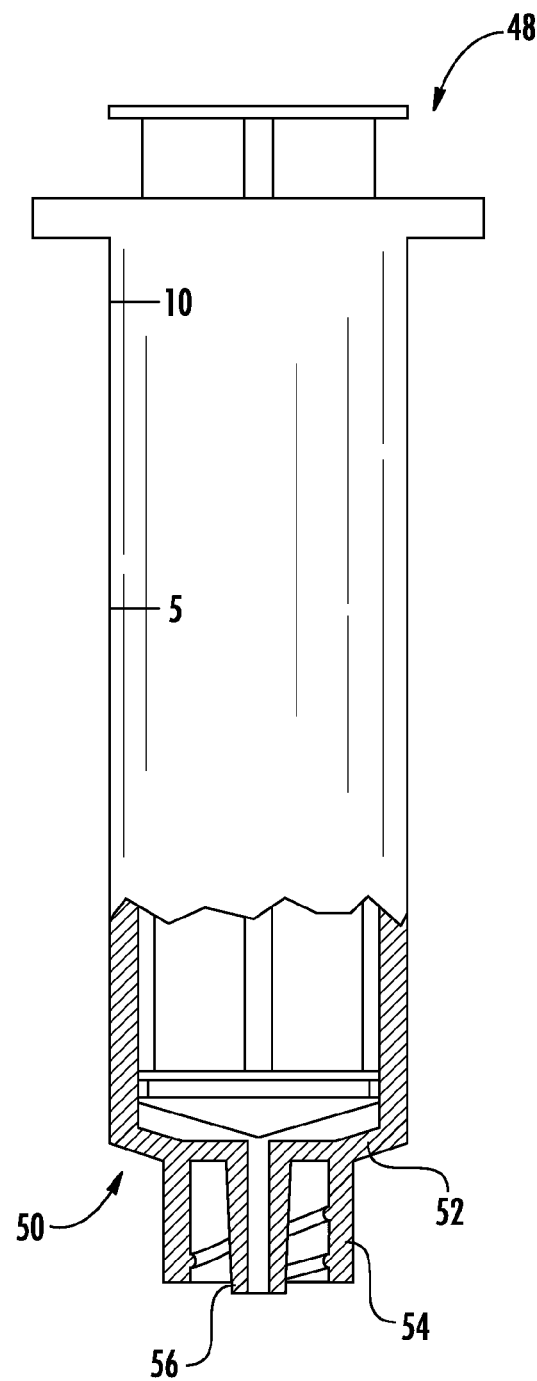
FIG. 4 is a schematic partially-sectioned side view of another prior art syringe.

It is also noted that various syringes are available using the common end wall structure. For example, the syringe 10 shown in FIG. 1 has a fluid capacity of approximately 60 mL (2 ounces). FIG. 4 illustrates an example of a different syringe 48 having a fluid capacity of approximately 10 mL (0.35 ounces) and including an end wall structure 50 with a conical end wall 52, needle boss 54 and needle fitting 56. This syringe 48 has the same angle of its end wall 52 as the end wall 16 of the syringe 10 shown in FIG. 1, and dimensions of the remainder of the end wall structure 50, i.e. the dimensions of the needle boss 54 and the needle fitting 56, are identical to those of the needle boss 18 and needle fitting 20 described above. It will therefore be understood that the same needle assembly 28 shown in FIG. 2 may be coupled to either of the syringes 10 or 48 shown in FIG. 1 or FIG. 4, respectively.

Figure 6:
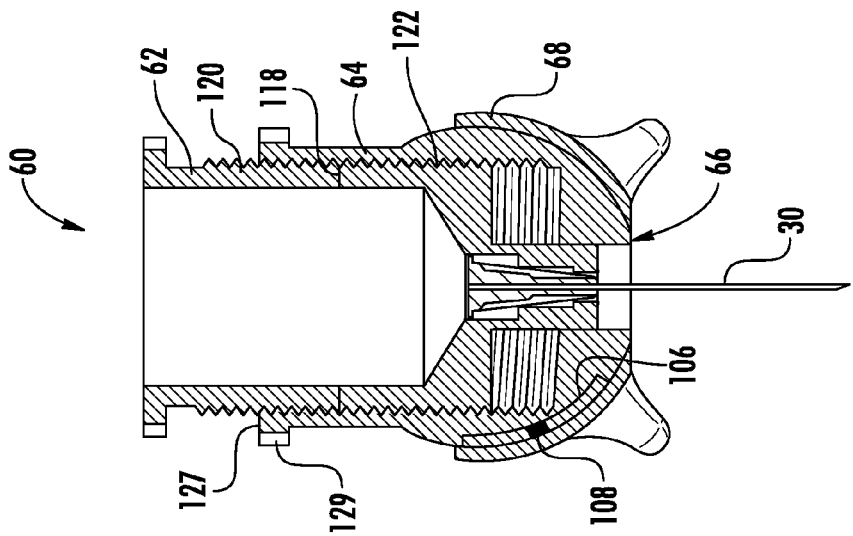
FIG. 6 is a cross-sectional view of the syringe guide of FIG. 5.
Figure 5:
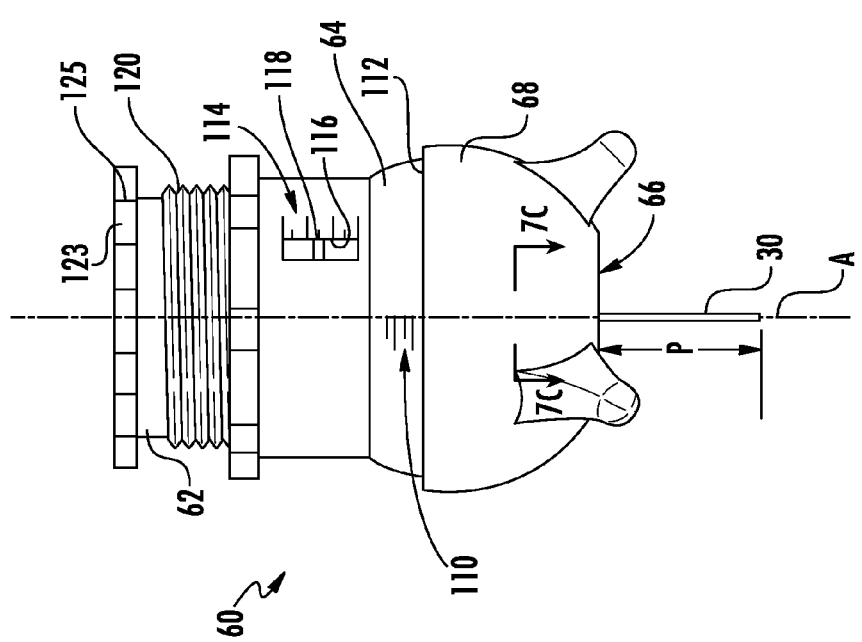
FIG. 5 is a side elevation view of an exemplary syringe guide.

FIGS. 5 and 6 illustrate an exemplary syringe guide 60 which may be used with either of the syringes described above, or any other syringe of similar configuration. The basic components of the syringe guide 60 are a syringe receiver 62 which receives and holds a syringe, a depth guide 64 which provides a reference surface 66, and optionally a base 68 which provides an enlarged bottom. For reference purposes a central axis "A" defines an axial or longitudinal direction of the syringe guide 60. A depth adjustment mechanism is also provided which varies the axial distance between the reference surface 66 and the syringe receiver 62. Each of these components will be described in detail below.

Figures 7A, 7B, 7C:
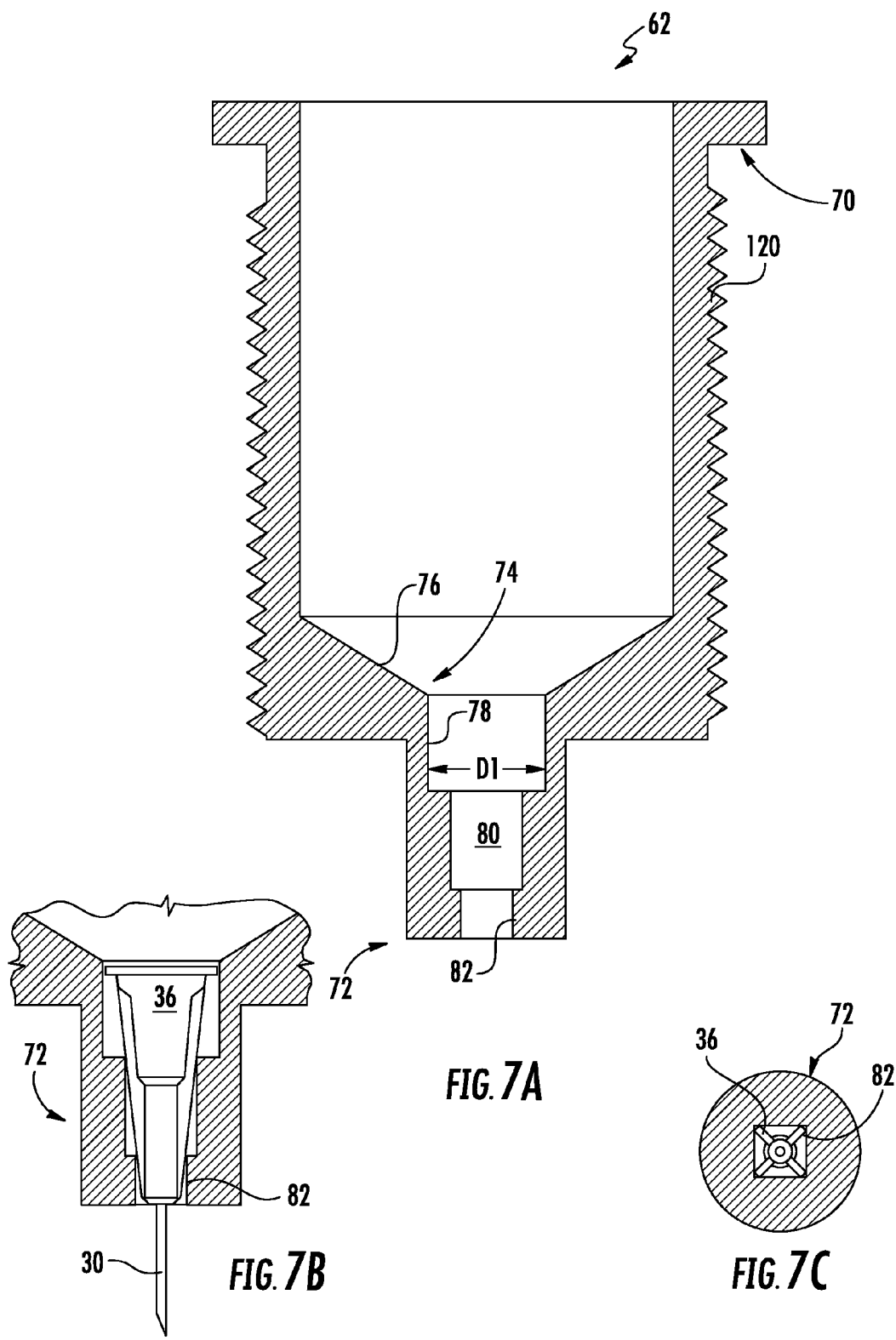
FIG. 7A is a cross-sectional view of a syringe receiver of the syringe guide of FIG. 5.
FIG. 7B is a cross-sectional view of the syringe receiver of FIG. 7A with a needle and need hub inserted therein.
FIG. 7C is a cross-sectional view taken along lines 7C-7C of FIG. 5.

FIG. 7A illustrates the syringe receiver 62 in more detail. The syringe receiver 62 has an upper end 70 and a lower end 72. The lower end 72 of the syringe receiver 62 defines a receptacle 74 which is configured to receive and engage a syringe such as the syringe 10 described above. More specifically, an interior end wall 76 is configured with a cone angle matching the angle of the end wall 16 of the syringe 10. A counterbore 78 communicates with the interior end wall 76 and has a diameter D1 selected to receive the outer diameter of the needle boss 18. A distal passageway 80 is shaped and sized to receive the outer dimensions of the needle hub 36 described above. Optionally, a distal portion 82 of the distal passageway 80 may be shaped and sized in a way so as to apply torque to the exterior of the needle hub 36. In the illustrated example, as best seen in FIGS. 7B and 7C, the distal portion 82 of the distal passageway 80 has a square cross-sectional shape and is sized such that when the needle hub 36 is received in the distal portion 82, the needle hub 36 is held stationary against rotation relative to the syringe receiver 62.

Figure 8:
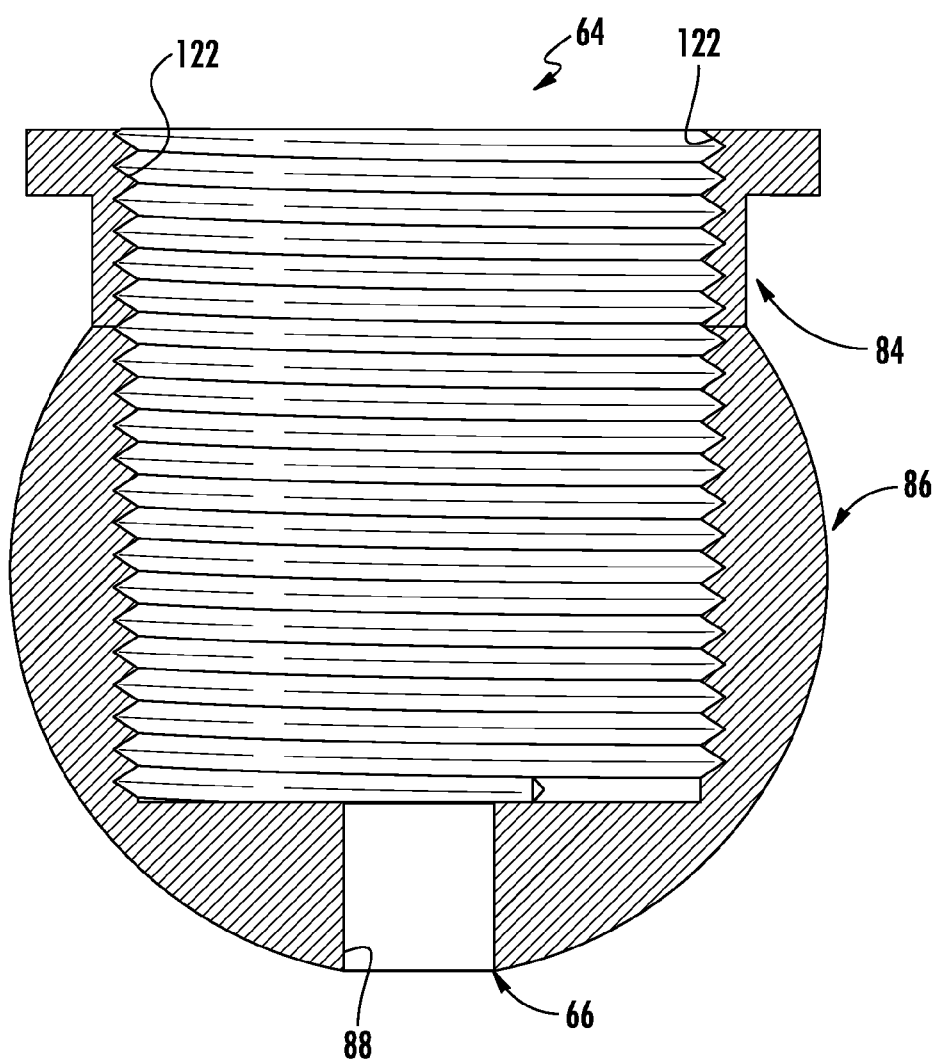
FIG. 8 is a cross-sectional view of a depth guide of the syringe guide of FIG. 5.

The depth guide 64 is shown in more detail in FIG. 8. The depth guide 64 is sized and shaped so as to be connected to the syringe receptacle 62 and includes upper and lower portions 84, 86. In the illustrated example, the upper portion 84 of the depth guide 64 is generally cylindrical and sized to receive the syringe receiver 62 therein.

The depth guide 64 defines the reference surface 66. In the illustrated example, the lower portion 86 of the depth guide 64 has a generally spherical shape, a portion of which defines the reference surface 66. A clearance hole 88 passes through the lower portion 86.

In the illustrated example, a small portion of the spherical shape is flat or planar where the spherical shape intersects the clearance hole 88. The small flat area defines the functional portion of reference surface 66. Other shapes are possible for the base of the depth guide 64. For example, the spherical shape could be truncated to a greater degree so a larger flat reference surface is provided. The greater the surface area of the reference surface 66, the more reliability in depth setting, but the less flexibility to modify an injection angle, as described in more detail below.

Figure 9:
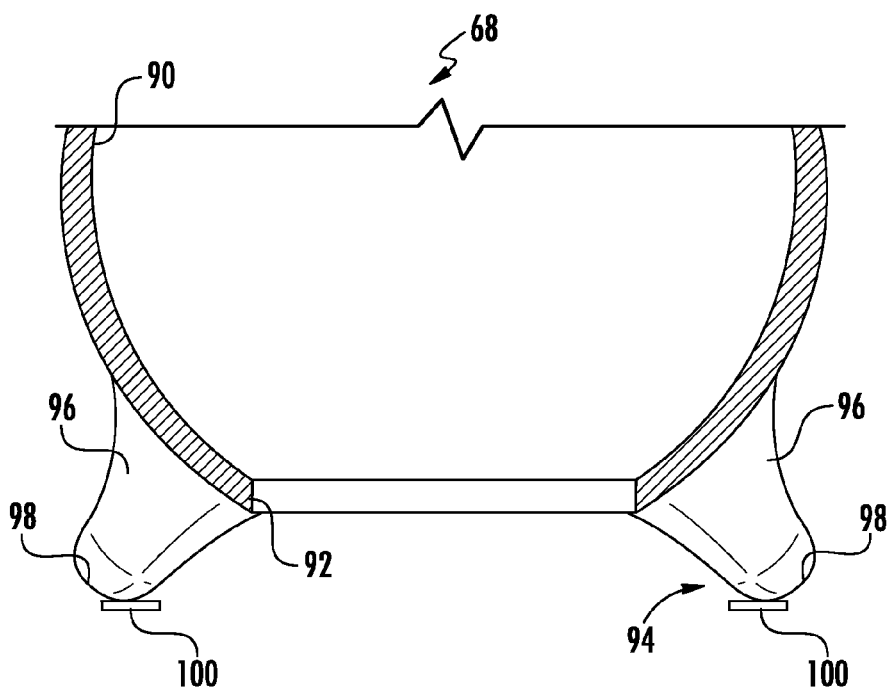
FIG. 9 is a cross-sectional view of a base of the syringe guide of FIG. 5.

The base 68 is illustrated in more detail in FIG. 9. The base 68 is configured to be coupled to the depth guide 64. In the illustrated example, the base has a generally spherically-shaped socket 90 formed therein. This socket 90 is shaped and sized so as to define a friction fit and/or snap fit with the lower portion 86 of the depth guide 64. The tightness of friction fit between the depth guide 64 and the base 68 can be altered to suit the requirements of a specific application. A clearance window 92 is formed through the base 68 to provide clearance for the needle assembly 28. When assembled as shown in FIG. 5, the depth guide 64 can pivot relative to the base 68 such that the needle 30 is capable of sweeping through a conical shape, or stated another way, is capable of pivoting in an arc through an infinite number of planes.

The base 68 incorporates a support surface 94 which is configured to be placed against at least one aspect of a patient (i.e. a human or other animal body). In the illustrated example, the support surface 94 is defined by three feet 96 with rounded tips 98 arranged in a tripod configuration. Such a configuration is believed to be suitable to be placed against a convex-shaped body part, such as a kneecap or a hand.

Figure 10:
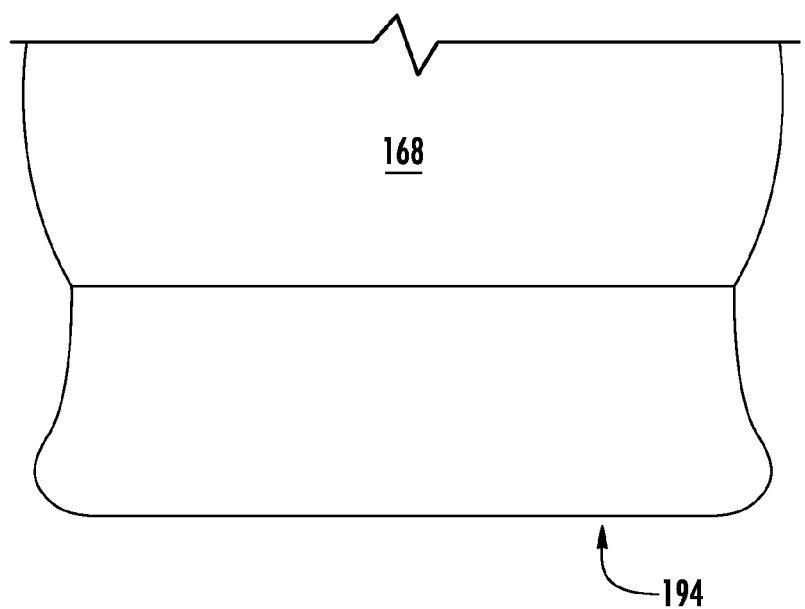
FIG. 10 is a side elevation view of an alternative base for a syringe guide.

Alternatively, the support surface 94 could be a different shape. For example, FIG. 10 depicts an alternative base 168 having a support surface 194 which is configured as a single, large-diameter disk or ring, which may be planar as illustrated, or have a convex or concave curvature. The greater the surface area of the support surface 194, the more reliability in depth setting, but the less flexibility to modify an injection angle as described in more detail below.

Optionally, the base 68 could be provided with means for removably securing the base 68 to a patient. As used herein the term "removably securing" refers to any structure or device operable to connect the base 68 to a patient which permits the base to be subsequently disconnected from the patient without causing injury the patient. This will be especially helpful in circumstances such as guided biopsy. This would help the physician avoid exposure to radiation. It would also be helpful in procedures such as an epidural injection. In the example shown in FIG. 9, optional double-sided adhesive pads 100 are shown attached to the tips 98 of the feet 96.

Figure 11:
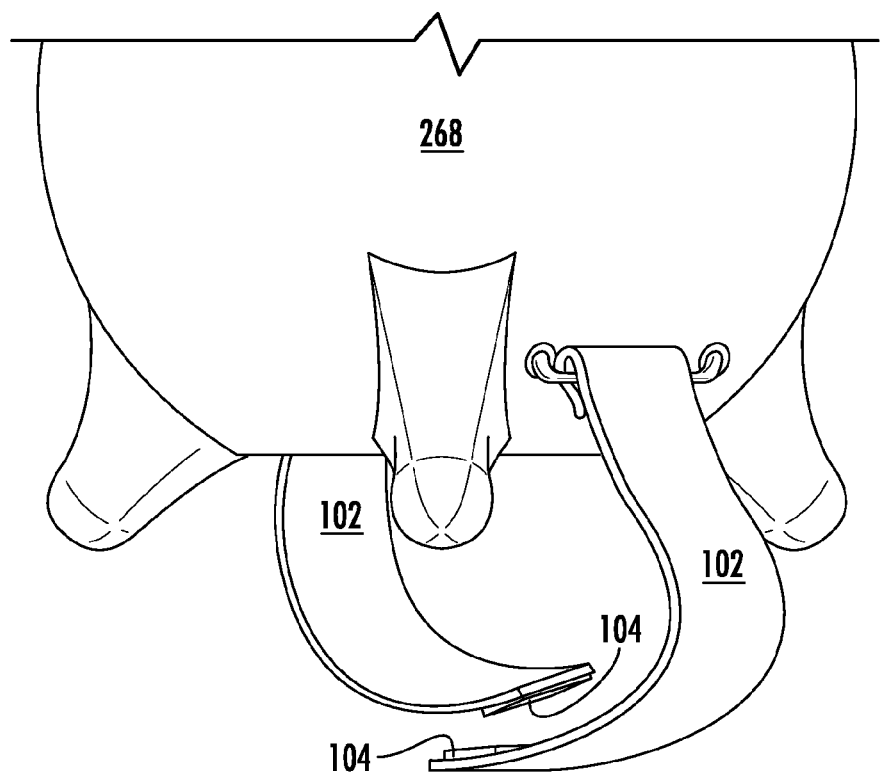
FIG. 11 is a side elevation view of an alternative base for a syringe guide, incorporating straps.

In another example shown in FIG. 11, an alternative base 268 is shown having straps 102 attached thereto. The straps may be wrapped around a body part such as a limb (not shown) and attached to each other with a fastener 104, such as a hook and loop material.

Optionally, means may be provided for guiding or limiting the pivoting motion of the depth guide 64. For example, FIG. 6 depicts a mutually engaged groove 106 in the depth guide 64 and tab 108 in the base 68 which permits the base 68 to pivot relative to the depth guide 64 in an arc lying in a single plane.

Optionally, markings may be provided showing the relative angular position of the depth guide 64 and the base 66. For example, FIG. 5 illustrates an angular scale 110 provided on the depth guide 64 which aligns with a top edge 112 of the base 68. As discussed further below, this type of marking may be useful in providing a predetermined position, or in repeating an existing position.

Optionally, markings may be provided showing the relative axial position of the syringe receiver 62 and the depth guide 64. For example, FIG. 5 illustrates a linear scale 114 provided on the depth guide 64 adjacent a slot 116 which permits viewing of a line 118 marked on the syringe guide 62. As discussed further below, this type of marking may be useful in providing a predetermined axial position, or in repeating an existing axial position.

The depth adjustment mechanism may be any mechanism which is operable to allow the distance between a reference point on the syringe receptacle 62 and the reference surface 64, parallel to axis A, to be adjusted to a desired value, and then set in position to prevent unintended movement. Non-limiting examples of suitable mechanisms include threaded mechanisms, gears or racks, rails, slots, or pins, friction or clamping mechanisms, or powered actuators.

In the example illustrated in FIGS. 5-7, the syringe receptacle 62 has male threads 120 formed thereon which engage female threads 122 formed in the depth guide 64. Relative rotation of the syringe receptacle 62 and the depth guide 64 thus causes the syringe receptacle 62 to advance or retract along the axis A relative to the reference surface 66. This has the result, when a syringe 10 is installed, of increasing or decreasing a protrusion "P" of the needle 30 beyond the reference surface 66. The pitch of the threads 120, 122 may be altered to provide a desired advance ratio. For example, if the pitch is 16 threads per inch, then each full 360° rotation of the syringe receptacle 62 relative to the depth guide 64 would advance or retract the needle 30 by approximately 1.6 mm (1/16 in).

To facilitate gripping and adjustment, the syringe receiver 62 may incorporate a flange 123 with gripping elements such as the illustrated tabs 125. The depth guide 64 may also incorporate a flange 127 with gripping elements such as illustrated tabs 129. In addition to facilitating a secure hand hold and application of torque, the provision of tabs 125, 129 may also serve as a convenient visual guide for counting turns or fractions of turns during an adjustment process.

Figure 12:
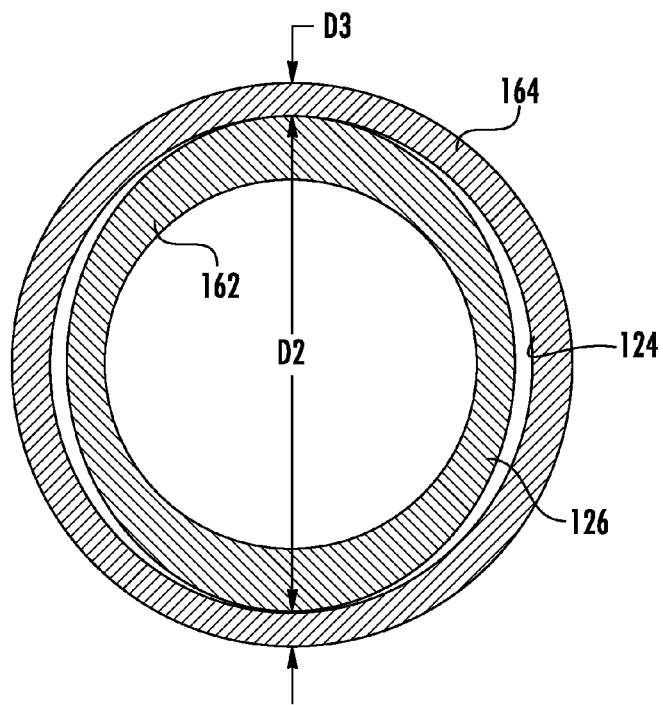
FIG. 12 is a cross-sectional view of an alternative syringe guide in a locked position.
Figure 13:
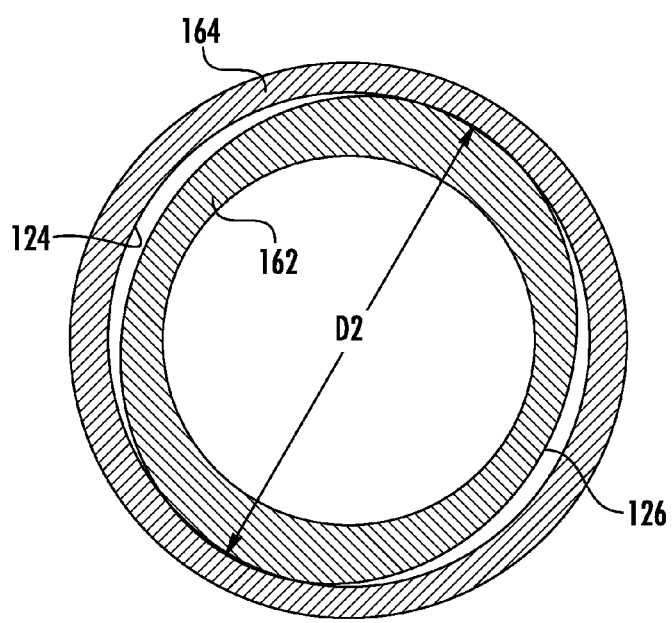
FIG. 13 is a cross-sectional view of the syringe guide of FIG. 12 in an unlocked position.

FIGS. 12 and 13 illustrate portions of an alternative syringe receptacle 162 and depth guide 164 which are generally similar to the syringe receptacle 62 and depth guide 64 described above, but which have an alternative depth adjustment mechanism. Specifically, the depth guide 164 includes an interior surface 124 which has an elliptical cross-sectional shape with the major diameter aligned with a first axis, shown oriented in a 12 o'clock position. The syringe receptacle 162 includes an exterior surface 126 which also has an elliptical cross-sectional shape. The shapes of the interior and exterior surfaces 124, 126 are selected such that in one orientation, there is a radial clearance between the syringe receptacle 162 and the depth guide 164, permitting sliding movement therebetween, and in another orientation there is friction and/or an interference fit between the syringe receptacle and the depth guide 164, preventing sliding movement therebetween.

As seen in FIG. 12, a major diameter D2 of the syringe receptacle 162 is aligned with the major diameter D3 of the interior surface 124. The major diameter D3 of the interior surface 124 is slightly larger than the major diameter D2 of the syringe receptacle 162. A radial clearance is thus present at all locations around the periphery of the syringe receptacle 162, and relative sliding motion to adjust the depth is possible.

As seen in FIG. 13, the syringe receptacle 162 has been rotated a fraction of a turn, in this case approximately 20°. The major diameter D2 of the syringe receptacle 162 frictionally engages and/or interferes with the interior surface 124. In this position, the two components are locked and the syringe receptacle 162 cannot be moved axially.

Figure 14:
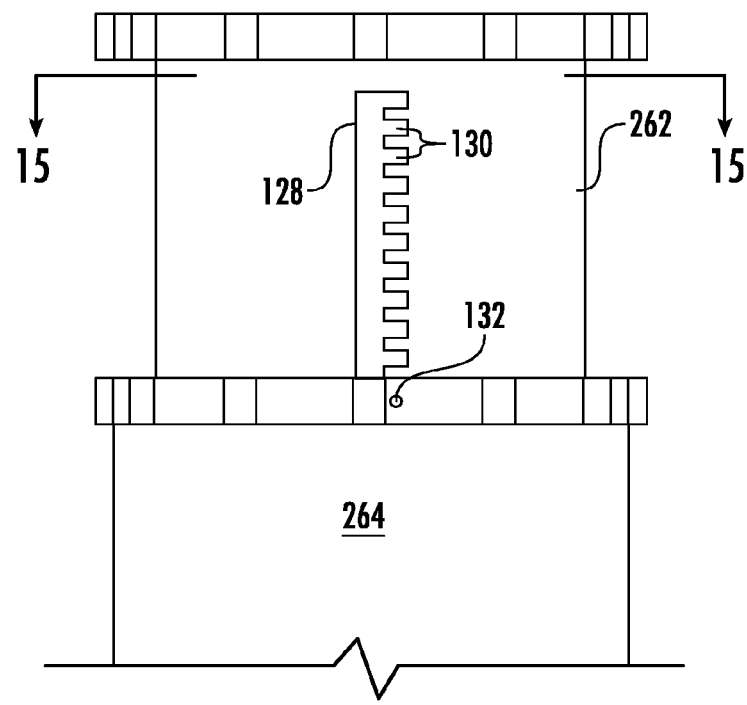
FIG. 14 is a side view of an alternative syringe guide.
Figure 15:
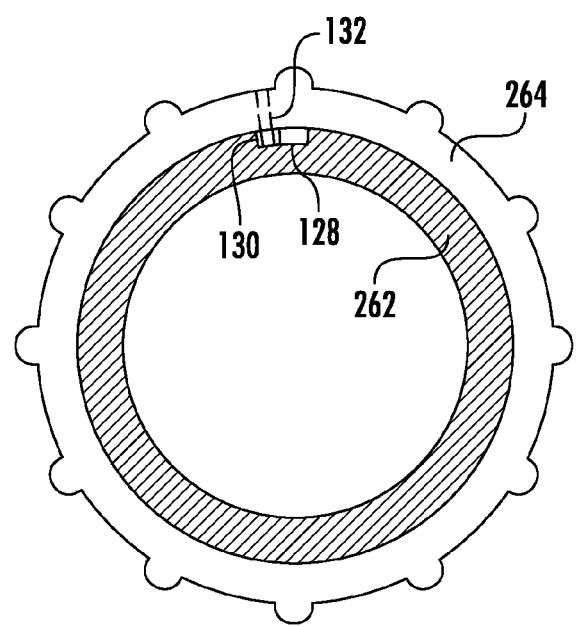
FIG. 15 is a view taken along lines 15-15 of the syringe guide of FIG. 14.

FIGS. 14 and 15 illustrate portions of an alternative syringe receptacle 262 and depth guide 264 which are generally similar to the syringe receptacle 62 and depth guide 64 described above, but which have an alternative depth adjustment mechanism. Specifically, the syringe receptacle 262 includes a longitudinal groove or keyway 128 formed in its exterior surface, with a plurality of laterally-extending notches 130 spaced along its length. The depth guide 264 includes a feature which extends radially inward and is engaged with the keyway 128, for example the illustrated pin 132. In the position shown in FIGS. 14 and 15, the pin 132 is engaged with one of the notches 130 thereby preventing axial movement of the depth guide 264 relative to the syringe receiver 262. By rotating the depth guide 264 a fraction of a turn, the pin 132 will disengage the notch 130 permitting axial movement. The depth guide 264 can then be slid into a new position, and turned back to a fraction of a turn to engage another notch 130.

The syringe guide 60 described above and all of its constituent components may be made from any material or combination of materials having the requisite strength and other material properties needed to suit a particular application. Generally, the syringe guide 60 and its constituent components would be made from a rigid or semi-rigid material, such as a polymer or a metal.

In some applications it may be desirable to make the syringe guide or some of its constituent components from a material that can be initially sterilized (i.e. produced in a sterile condition) or re-sterilized (e.g. sterilized using an autoclave, ultraviolet light, or other similar sterilization process). Examples of such materials include medical grade polymers, and metal alloys such as stainless steel.

All or part of the syringe guide 60 may be made wholly or partially transparent to one or more wavelengths of radiation in order to facilitate its use. For example, all or part of the syringe guide 60 may be made wholly or partially transparent to X-rays or other penetrating radiation (i.e. "radiotranslucent" or "radiotransparent") so that it can be used during an imaging process such as an X-ray process. Nonlimiting examples of X-ray processes include CAT scans and CT-guided biopsies.

As another example, all or part of the syringe guide 60 may be made wholly or partially transparent to visible light (i.e. "translucent" or "transparent"). For example, the depth guide 64 may be made transparent so that a user is able to see the needle 30 while the syringe guide 60 is in use.

The syringe guide 60 may be employed using multiple techniques to improve the accuracy and consistency of utilization of the syringe 10. Some examples of these uses will be described below.

There are two basic categories of use of the syringe guide 60: first, those in which a syringe 10 is used to inject a fluid, and second, those in which a syringe 10 is used to remove a fluid.

To inject a fluid, a syringe 10 is fitted with a needle assembly 28 and loaded with a fluid. The syringe 10 may be provided in a pre-filled condition, or the plunger 26 may be used to draw in fluid from a container, through the needle assembly 28. The loaded syringe 10 is placed into the syringe receiver 62. As noted above, the syringe receiver 62 is configured to engage the end wall structure 14 of the syringe 10. Specifically, the syringe 10 engages the interior end wall 76 and/or the counterbore 78. Thus a single syringe receiver 62 is suitable to securely receive multiple sizes of syringes 10. Once the syringe 10 is secured, the depth guide 64 is adjusted to a position that provides the correct protrusion of the needle 30. The depth of insertion of the needle 30 into a patient is limited by the reference surface 66. One or multiple injections may then be administered with confidence that the needle depth is correct.

To remove a fluid, a syringe 10 is fitted with a needle assembly 28 and the empty syringe 10 is placed into the syringe receiver 62. The depth guide 64 is adjusted to a position that provides the correct protrusion of the needle 30.

The needle 30 may then be inserted into a patient and the plunger 26 retracted to draw fluid into the syringe 10. In many instances, it may be necessary to withdraw more fluid than the capacity of the syringe 10. In these circumstances, the syringe guide 60 enables the user to remove and replace the syringe 10 without withdrawing the needle 30. To accomplish this, the syringe guide 60 is held in place while unscrewing the syringe 10. As described above, the syringe receiver 62 engages the needle hub 36 so that a torque can be applied to disengage the tabs 44 from the threads 46, pushing the needle fitting 20 away from the hub 36. Once the needle fitting 20 is free of the needle hub 36, the syringe 10 can be pulled away and either emptied or discarded. Subsequently, an empty syringe 10 can be placed back into the syringe receiver 62 and rotated to engage the tabs 44 with the threads 46, drawing the needle fitting 20 into the hub 36. The syringe 10 is then ready to withdraw additional fluid. This process can be repeated as many times as necessary.

The base 68 may be used to expand the functionality of the syringe guide 60. To use the base 68, it is attached to the depth guide 64 as described above, for example by snapping the two parts together. The support surface 94 of the base 68 then functions as a reference surface for the amount of protrusion of the needle 30.

In one application, the support surface 94 would be set perpendicular to the needle 30, and then usage of the device would be identical to the example described above. Stability of the device is enhanced using the base 68. For example, the feet 96 are useful in locating the syringe guide 60 on a convex-curved aspect of the body such as a knee. As another example, the alternative base 168 could be used to provide support over a large flat area of the patient body.

Figure 16:
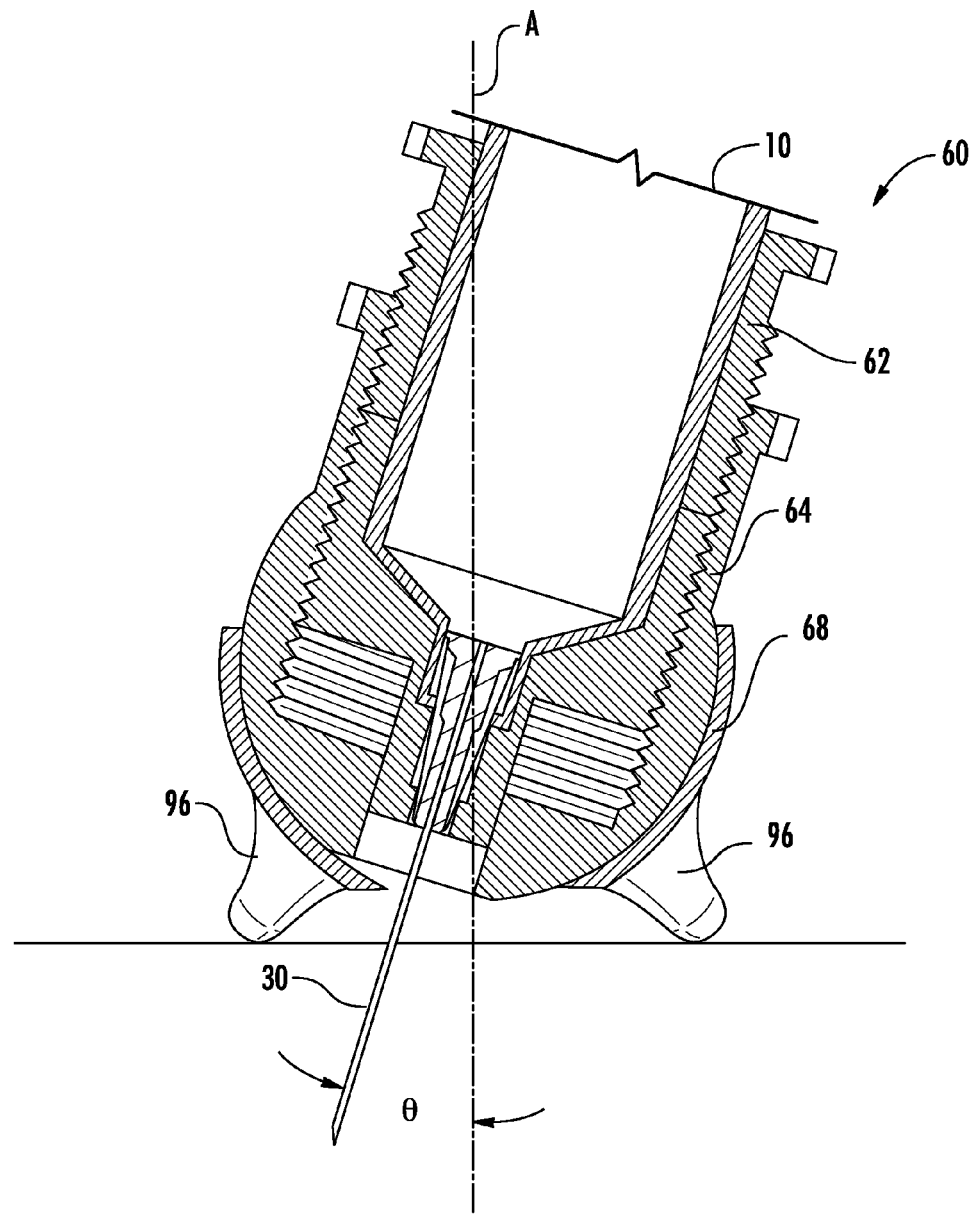
FIG. 16 is a cross-sectional view of the syringe guide of FIG. 5 in a tilted position.

In another application, the base 68 may be pivoted away from perpendicular to the needle 30 as needed to facilitate a specific procedure. FIG. 16 shows the syringe guide 60 tilted at an angle θ to the axis A. For example, the base 68 may be pivoted in order to allow the needle 30 to penetrate a patient body normal to the surface while allowing the feet 96 to securely engage the body and stabilize the syringe guide 60.

In another application, the base 68 may be pivoted in order to adjust the position of the needle 30 or to move the needle 30 between a sequence of punctures. For example, if the base 68 is attached to a patient and a nominal location using the adhesive pads 100 or straps 102 described above, the needle 30 may not be aligned with the desired location to penetrate the patient. This may be corrected by pivoting the syringe receiver 62 and depth guide 64 relative to the base 68, thereby moving the tip of the needle 30, without having to remove the base 68 from the patient.

As another example, the base 68 may be attached to the patient at a nominal location using the adhesive pads 100 or straps 102 described above with the needle 30 aligned at an initial injection point. A first injection may then be carried out. A second injection may be carried out at a nearby location by pivoting the syringe receiver 62 and depth guide 64 relative to the base 68, thereby moving the tip of the needle 30 to a new location.

Any of the procedures described above may be used in conjunction with the angular markings described above. For example, the angular scale 110 described above may be used to preset an angular position of the depth guide 64 relative to the base 66 before carrying out a procedure. Alternatively, the angular scale 110 may be used as a reference to repeat a desired position. For example, if the syringe guide 60 is being used at a specific pivot angle, and the device should be removed from the patient, dropped, or accidentally pivoted away from the desired angle, it could be reset to the previous position by referencing the angular scale 110.

Any of the procedures described above may also be used in conjunction with the linear markings described above. For example, the linear scale 114 described above may be used to preset an axial position of the syringe receiver 62 relative to the depth guide 64 before carrying out a procedure. Alternatively, the linear scale 114 may be used as a reference to repeat a desired position. For example, if the syringe guide 60 is being used at a specific axial position, and the device should be removed from the patient, dropped, or accidentally adjusted, it could be reset to the previous position by referencing the linear scale 114.

It is noted that the protrusion P of the needle 30 and the axial position of the syringe receiver 62 both move in unison, so any change on a linear scale 114 will result in a 1:1 change in the protrusion P. However, as noted above, needles 30 are available in various lengths. Therefore, a specific scale setting may not necessarily correspond to a specific protrusion P. To facilitate use of the device, it is possible to provide a chart or tabulated data which correlates specific scale indications (length and/or angle) to specific needle protrusions P, for specific needle lengths.

FIGS. 17A-17D illustrate another use for the syringe guide 60, namely guiding insertion of a flexible instrument such as a wire or catheter.

Figure 17A:
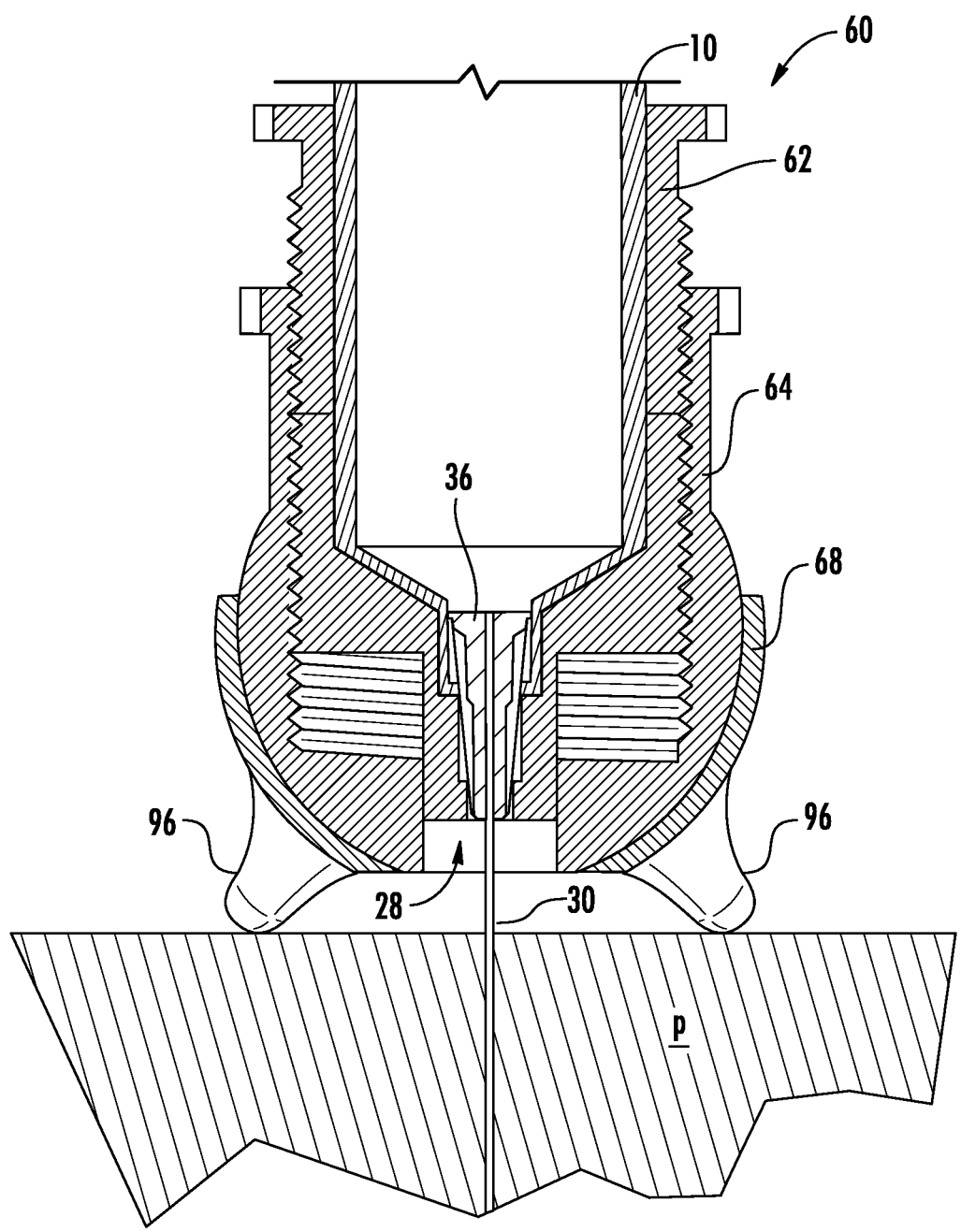
FIG. 17A is a cross-sectional view of a syringe guide being used with a syringe to insert a needle into a patient.

To begin the procedure, a syringe 10 is fitted with a needle assembly 28 and the empty syringe 10 is placed into the syringe receiver 62 (see FIG. 17A). The depth guide 64 is adjusted to a position that provides the correct protrusion of the needle 30. The needle 30 is introduced into a patient "p", for example the needle 30 may be introduced into a blood vessel. The syringe 10 may be used to aspirate the vessel to confirm accurate needle position.

Figure 17B:
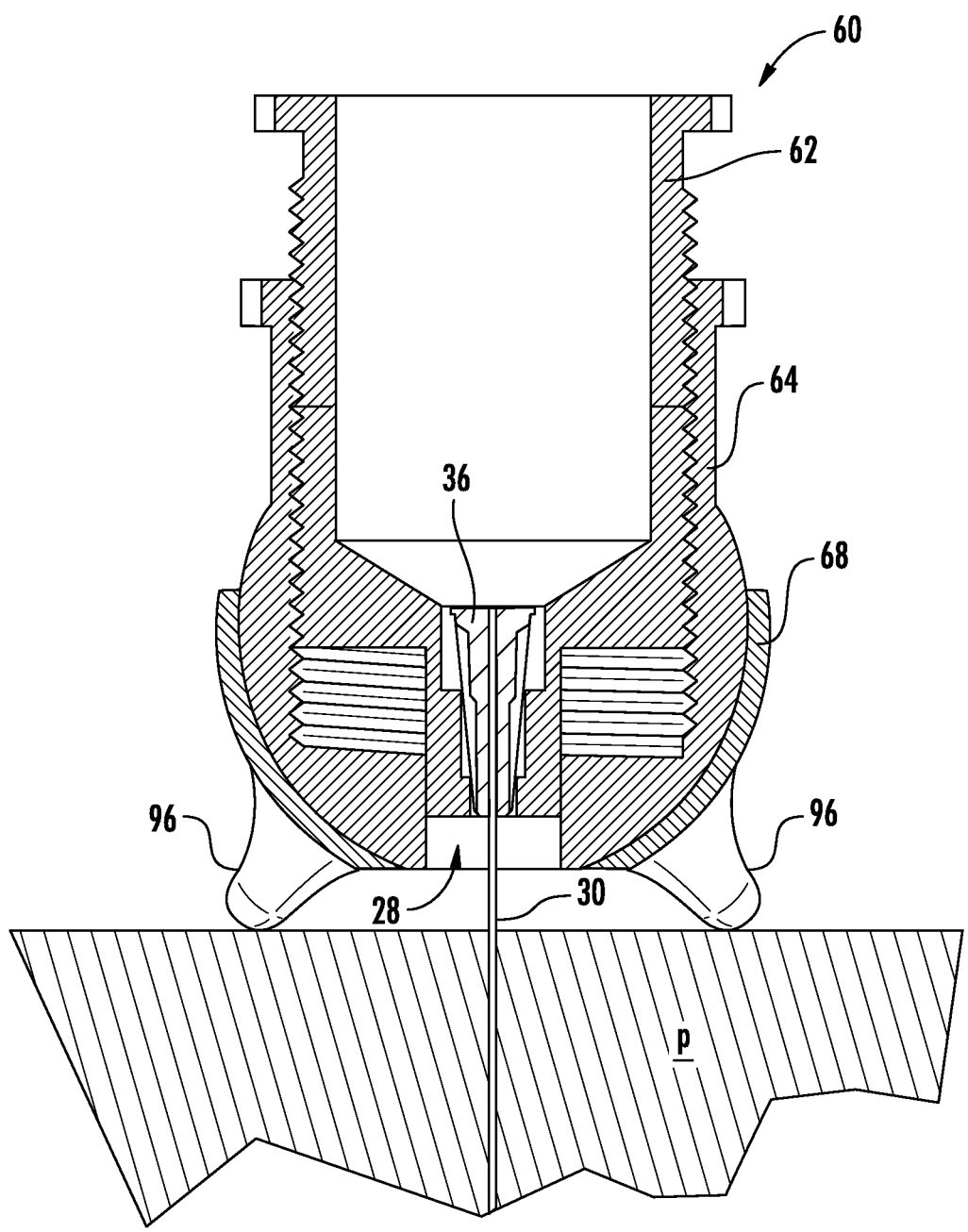
FIG. 17B is a cross-sectional view of the syringe guide after removal of the syringe.

Next, the syringe 10 is removed (see FIG. 17B). As described above, the syringe receiver 62 engages the needle hub 36 so that a torque can be applied to disengage the tabs 44 from the threads 46, pushing the needle fitting 20 away from the hub 36. Once the needle fitting 20 is free of the needle hub 36, the syringe 10 can be pulled away.

Figure 17C:
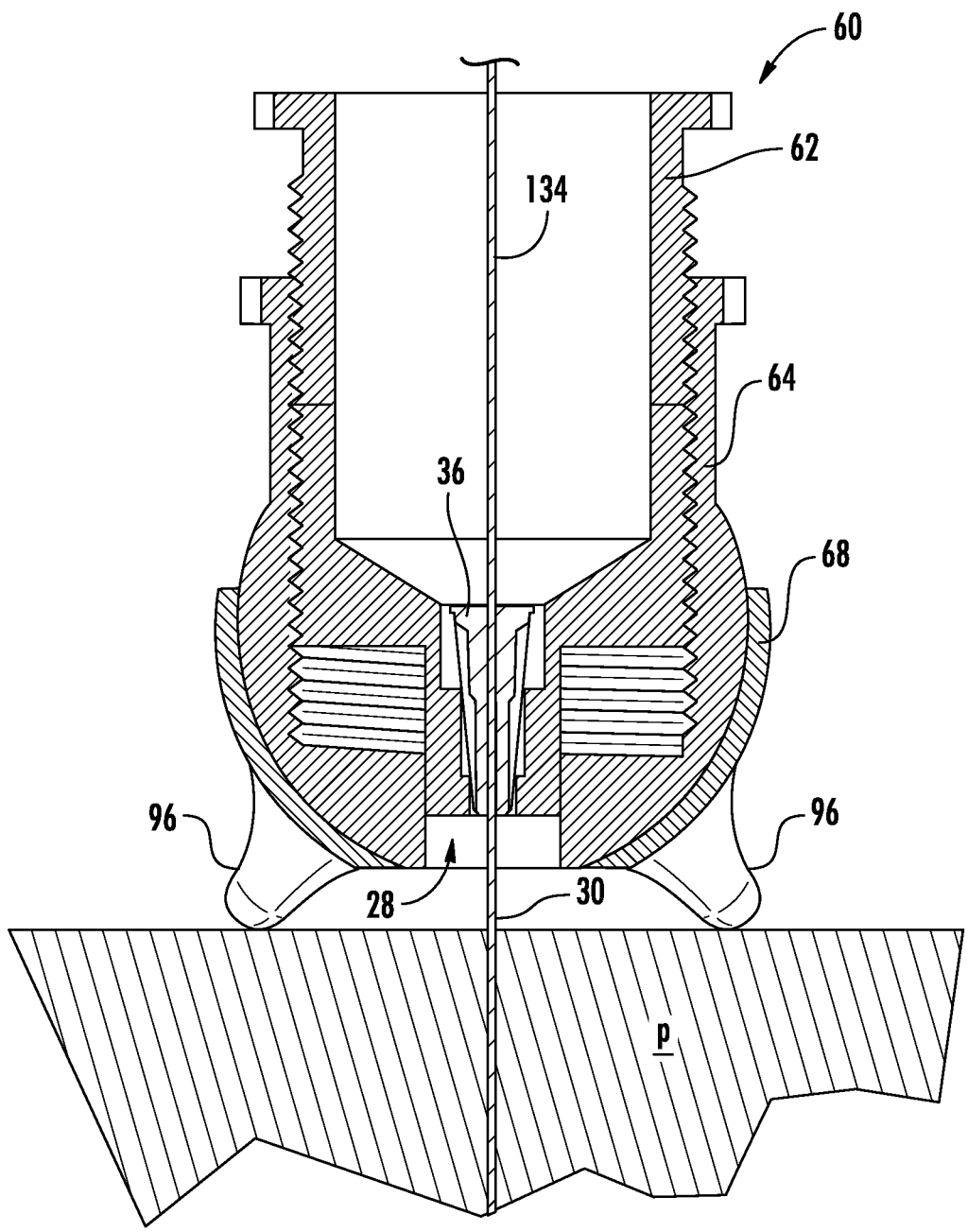
FIG. 17C is a cross-sectional view of the syringe guide of FIG. 17A being used to insert a wire through the needle and into the patient.
Figure 17D:
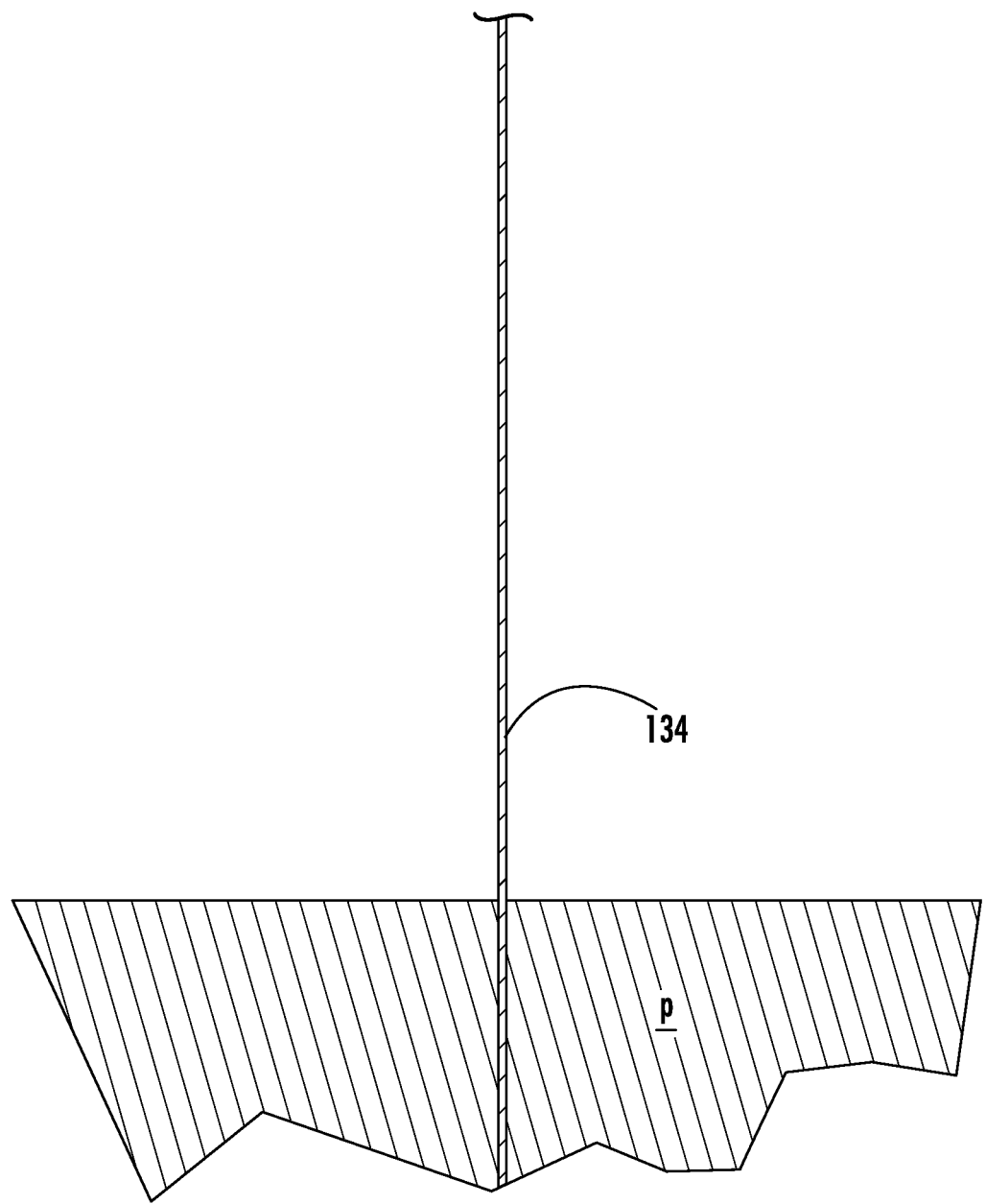
FIG. 17D is a cross-sectional view of the wire inserted into the patient after the removal of the syringe and syringe guide.

A wire or catheter 134 is then threaded through the needle 30 and into the patient p (FIG. 17C). Once the wire or catheter 134 is in place, the needle 30 can be removed (FIG. 17D) and the procedure continued.

The syringe guide 60 described herein is particularly useful in overcoming problems in difficult syringe use situations. Some examples are as listed below.

While drawing off fluid from a joint (a knee for example) the syringe 10 is changed after the local anesthetic is administered. In the prior art this is carried out by reaching down with the non-dominant hand, grasping the needle hub 36 and hoping that as you twist to remove it, it isn't inadvertently removed from the patient. In contrast, the syringe guide 60 allows for the use of the existing needle already through the skin or to keep the entry point the same and change needles. Similarly the syringe 10 can be exchanged or "swapped out" without removing the needle at all. Needle advancement is slow and controlled. The depth guide 64 and/or base 68 stabilizes the needle placement and minimizes over penetration should the patient flinch or move. It captures the needle hub 36 and allows a larger syringe 10 to be attached without withdrawing the needle 30.

The depth limiting function can be used to prevent over penetration of a needle, as in an intramuscular injection. Patient body habitus, body mass index ("BMI") or other measures can be used to accurately target the intended tissue. Subcutaneous fat can be avoided when the target is muscle. Furthermore it allows for a single pointed prick eliminating the need to feel around with the needle itself, causing patient discomfort. The depth limiting function is also useful for subcutaneous injections which occur at a very shallow depth.

As another example, the smallpox vaccine is administered by pricking the skin 15 times or more to get a good "take" of the vaccine. In the prior art, this procedure is frequently done incorrectly. After the first few pricks the patient retracts and depth varies widely. In contrast, using the syringe guide 60 facilitates comfortable repeat punctures. For example, this may be done by removing the base 68 and using the reference surface 66 of the depth guide 64 to permit repeated punctures at a fixed depth.

As another example, collagenase injections (e.g. brand name XIAFLEX) are used to dissolve a band of pathologic tissue in the hand, foot or penis. The bioengineered enzyme dissolves the cord but can damage normal tissue if misplaced. Most commonly used for Dupuytren's contracture in the hand it has become a mainstay of treatment. There is a need for very precise placement of this substance through a very small diameter needle. The syringe guide 60 permits repeat injections at fixed or varied depths. It also permits the needle 30 to be moved so as to follow a line along the skin by pivoting the syringe receiver 62, without moving the entire syringe guide 60.

Other typical applications of the syringe guide 60 include, but are not limited to: fine needle biopsy and aspiration; placement of intravascular wires for catheter placement targeting of intraosseous catheters in a trauma setting; mass sampling, allowing sequential depth biopsy from one needle stick; percutaneous needle decompression of pneumothorax by allowing for gradual depth increase with fine advancement while under duress; cyst/ganglion aspiration; suprapubic catheter placement; pleurocentesis; amniocentesis; paracentesis; and intracranial pressure monitor placement.

The syringe guide 60 described herein has several advantages over prior art devices and methods. It allows for a stable platform that has the ability to house several sizes of syringes, allows for accurate angular and depth delivery of medicine and similarly allows for the aspiration of fluid from the same location by the ability to remove the empty (or full) syringe while leaving the needle in place and subsequently replacing the empty (or full) syringe.

The syringe guide 60 provides an adjustable support apparatus to deliver medicine in a strategic location as well as a strategic depth with accuracy and stability.

The foregoing has described a syringe guide and methods for its use. All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

What is claimed is:

1. A syringe guide comprising:
   a syringe receiver including a receptacle configured to retain a syringe therein;
   a depth guide defining a reference surface;
   a depth adjustment mechanism interconnecting the syringe receiver and the depth guide, and operable to change a distance between the receptacle and the reference surface; and
   a base defining a support surface coupled to the depth guide, wherein the depth guide includes a spherical outer surface, and the base includes a spherical inner surface which receives the outer surface such that the base is pivotable relative to the depth guide.

2. The syringe guide of claim 1 wherein the depth adjustment mechanism has a first position which permits sliding movement between the syringe receiver and the depth guide, and a second position which prevents sliding movement between the syringe receiver and the depth guide.

3. The syringe guide of claim 1 further comprising means for limiting the pivoting motion of the depth guide relative to the base, to an arc lying in a single plane.

4. The syringe guide of claim 1 wherein the base includes a plurality of feet protruding therefrom.

5. The syringe guide of claim 1 wherein the base includes a flat circular surface.

6. The syringe guide of claim 1 wherein the base includes an adhesive material attached thereto.

7. The syringe guide of claim 1 wherein the base includes at least one strap attached thereto.

8. The syringe guide of claim 1 wherein at least one of the syringe receiver, the depth guide, and the base is partially or wholly transparent to one or more wavelengths of radiation.

9. The syringe guide of claim 1 wherein the depth adjustment mechanism comprises threads formed on the syringe receiver engaged with threads formed on the depth guide.

10. The syringe guide of claim 1 wherein the depth adjustment mechanism comprises mutually engaging non-cylindrical surfaces formed on the syringe receiver and the depth guide.

11. The syringe guide of claim 1 wherein the depth adjustment mechanism comprises a mutually engaged groove and key.

12. A syringe guide, comprising:
a syringe receiver including a receptacle configured to retain a syringe therein:
a depth guide defining a reference surface;
a depth adjustment mechanism interconnecting the syringe receiver and the depth guide, and operable to change a distance between the receptacle and the reference surface;
wherein the syringe receiver further comprises a receptacle configured to retain a taper-fit needle hub via friction fit in a distal passageway of the syringe receiver, such that a syringe barrel may be connected to or disconnected from the taper-fit needle hub while the needle remains in place in the syringe receiver.

13. The syringe guide of claim 12 wherein the receptacle is configured such that the needle hub is sufficiently retained such that the syringe can be replaced while a needle remains in a patient.

14. The syringe guide of claim 1 wherein the syringe receiver comprises markings which indicate the depth of the needle or position of the depth adjustment mechanism.

15. The syringe guide of claim 1 comprising material that can be sterilized.

16. The syringe guide of claim 1 comprising material that can be resterilized.

17. The syringe guide of claim 12 wherein the depth adjustment mechanism has a first position which permits sliding movement between the syringe receiver and the depth guide, and a second position which prevents sliding movement between the syringe receiver and the depth guide.

18. The syringe guide of claim 12 further comprising a base defining a support surface coupled to the depth guide.

19. The syringe guide of claim 18 wherein:
the depth guide includes a spherical outer surface; and
the base includes a spherical inner surface which receives the outer surface such that the base is pivotable relative to the depth guide.

20. The syringe guide of claim 18 wherein the base includes a plurality of feet protruding therefrom.

21. The syringe guide of claim 18 wherein the base includes a flat circular surface.

22. The syringe guide of claim 18 wherein the base includes an adhesive material attached thereto.

23. The syringe guide of claim 18 wherein the base includes at least one strap attached thereto.

24. The syringe guide of claim 12 wherein at least one of the syringe receiver and the depth guide is partially or wholly transparent to one or more wavelengths of radiation.

25. The syringe guide of claim 12 wherein the depth adjustment mechanism comprises threads formed on the syringe receiver engaged with threads formed on the depth guide.

26. The syringe guide of claim 12 wherein the depth adjustment mechanism comprises mutually engaging non-cylindrical surfaces formed on the syringe receiver and the depth guide.

27. The syringe guide of claim 12 wherein the depth adjustment mechanism comprises a mutually engaged groove and key.

* * * * *